United States Patent
Forthmann et al.

(10) Patent No.: US 8,180,017 B2
(45) Date of Patent: May 15, 2012

(54) STEREO TUBE ATTENUATION FILTER

(75) Inventors: Peter Forthmann, Sandesneben (DE); Roland Proksa, Hamburg (DE); Axel Thran, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 149 days.

(21) Appl. No.: 12/746,364

(22) PCT Filed: Dec. 12, 2008

(86) PCT No.: PCT/IB2008/055264
§ 371 (c)(1),
(2), (4) Date: Jun. 4, 2010

(87) PCT Pub. No.: WO2009/083848
PCT Pub. Date: Jul. 9, 2009

(65) Prior Publication Data
US 2010/0246756 A1    Sep. 30, 2010

Related U.S. Application Data

(60) Provisional application No. 61/015,392, filed on Dec. 20, 2007.

(51) Int. Cl.
*A61B 6/00* (2006.01)
*G21K 3/00* (2006.01)
(52) U.S. Cl. .......................................... 378/9; 378/156
(58) Field of Classification Search ............. 378/9, 156
See application file for complete search history.

(56) References Cited

U.S. PATENT DOCUMENTS

| | | | | |
|---|---|---|---|---|
| 4,696,022 A * | 9/1987 | Sashin et al. | | 378/41 |
| 5,625,661 A * | 4/1997 | Oikawa | | 378/15 |
| 6,256,369 B1 * | 7/2001 | Lai | | 378/14 |
| 6,754,299 B2 * | 6/2004 | Patch | | 378/15 |
| 6,879,655 B2 | 4/2005 | Proksa | | |
| 7,027,552 B2 | 4/2006 | Shechter | | |
| 7,042,975 B2 | 5/2006 | Heuscher | | |
| 7,142,628 B2 | 11/2006 | Grass et al. | | |
| 7,180,975 B2 | 2/2007 | Heuscher et al. | | |
| 7,187,747 B2 | 3/2007 | Bontus et al. | | |
| 7,292,717 B2 | 11/2007 | Kohler et al. | | |
| 7,433,443 B1 * | 10/2008 | Tkaczyk et al. | | 378/19 |
| 7,634,047 B2 * | 12/2009 | Popescu et al. | | 378/19 |
| 7,649,973 B1 * | 1/2010 | Li et al. | | 378/9 |
| 2002/0021780 A1 | 2/2002 | Kohler et al. | | |
| 2003/0128801 A1 | 7/2003 | Eisberg | | |
| 2003/0147502 A1 | 8/2003 | Heismann | | |
| 2003/0185345 A1 | 10/2003 | Hsieh | | |
| 2004/0081270 A1 | 4/2004 | Heuscher | | |
| 2004/0179646 A1 * | 9/2004 | Li et al. | | 378/19 |

(Continued)

FOREIGN PATENT DOCUMENTS

| | | |
|---|---|---|
| DE | 10237546 A1 | 3/2004 |
| WO | 0226134 A1 | 4/2002 |
| WO | 2006038142 A1 | 4/2006 |
| WO | 2007110793 A1 | 10/2007 |
| WO | 2008021661 A2 | 2/2008 |
| WO | 2008024586 A2 | 2/2008 |

*Primary Examiner* — Edward Glick
*Assistant Examiner* — Alexander H Taningco

(57) ABSTRACT

A computed tomography apparatus (10) includes spaced radiation sources (82, 84), such as anodes, which each propagate a cone-beam of radiation (40, 50) into an examination region (14). A detector (22) detects radiation which has passed through the examination region. An attenuation system (55) interposed between the radiation sources and the examination region for cone-angle dependent filtering of the cone beams. The attenuation system allows rays which contribute little to a reconstructed image to be attenuated more than rays which contribute more.

37 Claims, 7 Drawing Sheets

U.S. PATENT DOCUMENTS

| | | |
|---|---|---|
| 2005/0053189 A1* | 3/2005 | Gohno et al. ............ 378/16 |
| 2005/0135550 A1 | 6/2005 | De Man et al. |
| 2005/0190878 A1 | 9/2005 | De Man |
| 2005/0195935 A1* | 9/2005 | Yahata ................. 378/4 |
| 2006/0159220 A1* | 7/2006 | Heuscher ............... 378/9 |
| 2006/0262893 A1 | 11/2006 | Tang |
| 2006/0285633 A1* | 12/2006 | Sukovic et al. .......... 378/9 |
| 2007/0019776 A1 | 1/2007 | Bontus et al. |
| 2007/0177713 A1 | 8/2007 | Kohler et al. |

* cited by examiner

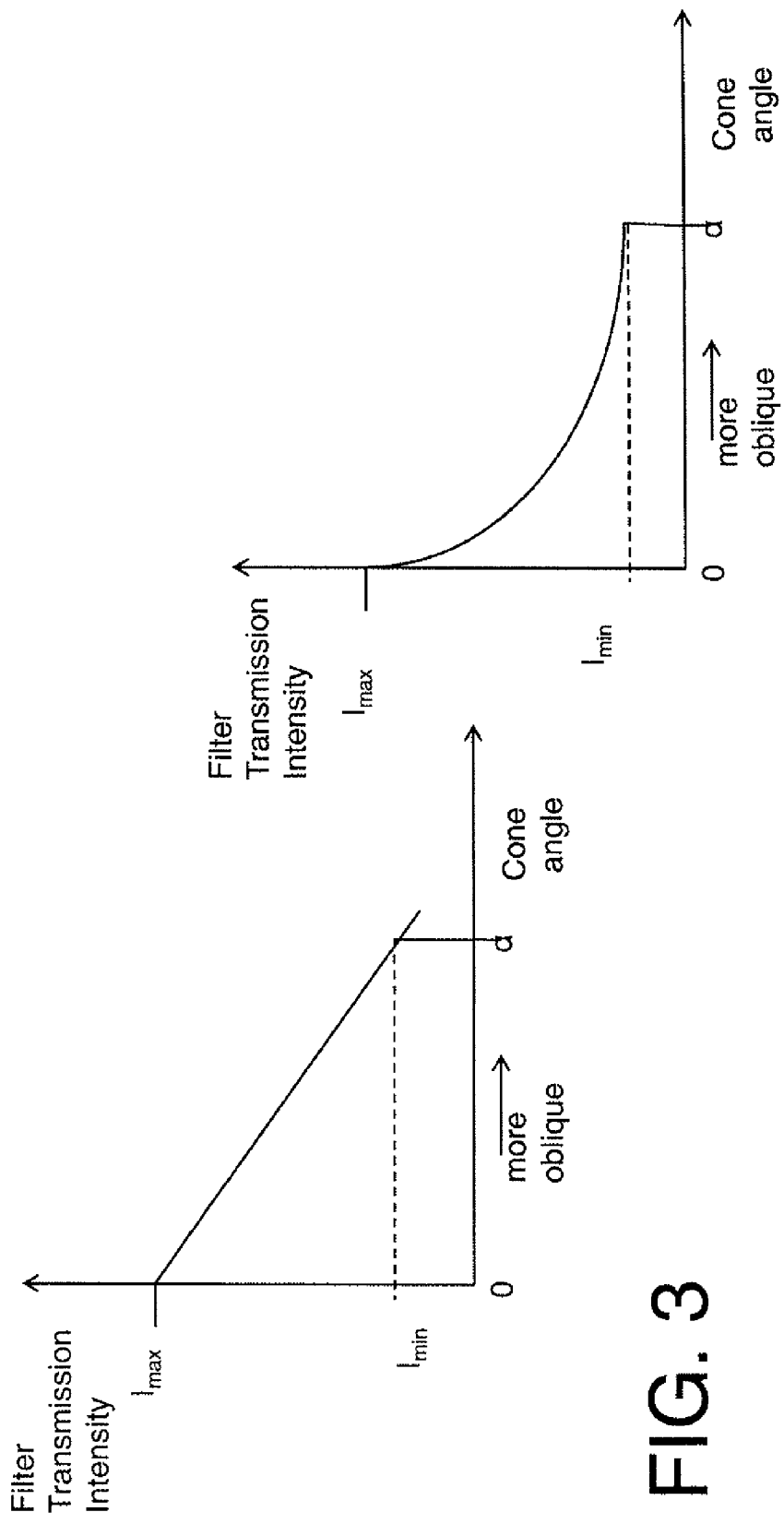

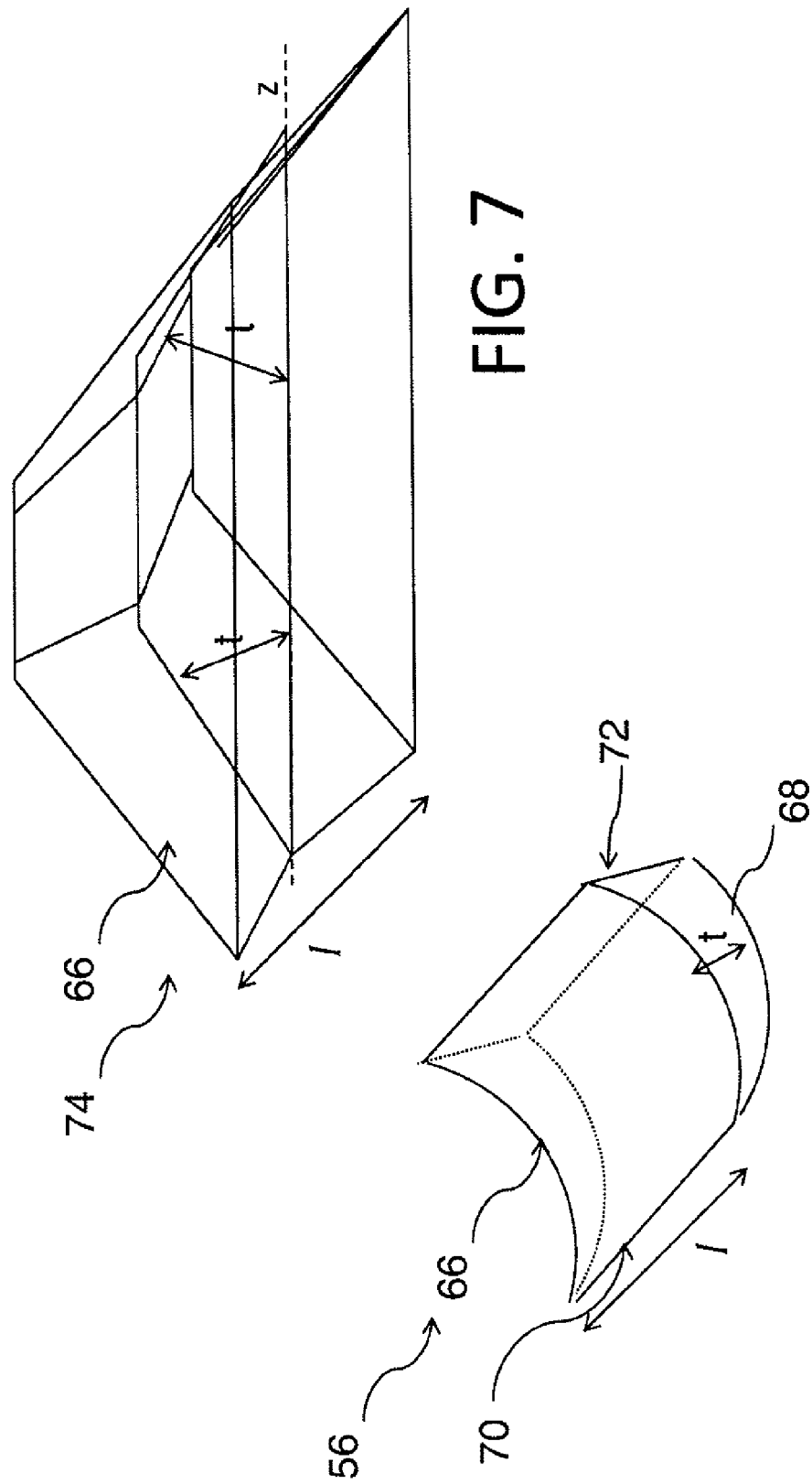

STEREO TUBE ATTENUATION FILTER

CROSS REFERENCE TO RELATED APPLICATIONS

This application claims the benefit of U.S. provisional application Ser. No. 61/015,392 filed Dec. 20, 2007, which is incorporated herein by reference.

The present application relates to computed tomography imaging. It finds particular application in connection with an attenuation system for variably filtering a beam of radiation so that in irradiating a subject, radiation which contributes little to a reconstruction of the imaging subject is attenuated.

In a typical computed tomography (CT) imaging apparatus, an x-ray tube is mounted on a rotating gantry that defines an examination region inside which an imaging subject is disposed. The x-ray tube rotates about the subject on the rotating gantry and projects a wedge-, fan-, cone-, or otherwise-shaped x-ray beam through the examination region. A two-dimensional x-ray detector disposed on the rotating gantry across the examination region from the x-ray tube receives the x-ray beam after passing through the examination region. Suitable electronics estimate x-ray absorption data based on the detected x-ray intensities, and an image reconstruction processor reconstructs an image representation based on the absorption data.

In cone-beam reconstruction methods, multiple rays (pi partners) eligible for backprojection through the same voxel are weighted according to their cone angle. Oblique rays are downweighted more strongly than less oblique rays. This leads to a mismatch in dose utility between these rays. The irradiated subject is thus unnecessarily fully exposed to rays that have little contribution to the final image.

The present application provides a new and improved apparatus and method which overcome the above-referenced problems and others.

In accordance with one aspect, a computed tomography apparatus includes spaced radiation sources which each propagate a cone-beam of radiation into an examination region. A detector detects radiation which has passed through the examination region. An attenuation system is interposed between the radiation sources and the examination region for cone-angle dependent filtering of the cone beams.

In accordance with another aspect, a method of computed tomography imaging includes projecting first and second cone beams of radiation towards an examination region and, prior to the examination region, attenuating the first and second cone beams to form attenuated first and second conebeams, the attenuation being dependent on a cone angle. Radiation data from the examination region is acquired.

In accordance with another aspect, an imaging apparatus includes a radiation source which propagates a cone-beam of radiation into an examination region. A detector detects radiation which has passed through the examination region. A filter, formed of a material which attenuates the radiation, is interposed between the radiation source and the examination region, the filter providing cone-angle dependent filtering of the cone beam, whereby more obliquely angled rays are filtered more than less obliquely angled rays.

One advantage is that a patient receives less exposure to x-rays that have little contribution to the final image.

Another advantage is that the radiation from a stereo x-ray tube is more evenly spread across the field of view in the scanning direction.

Still further advantages of the present invention will be appreciated by those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 3 is a schematic plot of x-ray intensity vs. cone angle for a cone-angle dependent filter in accordance with another aspect of the exemplary embodiment;

FIG. 4 is a schematic plot of x-ray intensity vs. cone angle for a cone-angle dependent filter in accordance with another aspect of the exemplary embodiment;

FIG. 6 is a perspective view of the cone-angle dependent filter of FIG. 2;

FIG. 7 is a perspective view of another embodiment of a cone-angle dependent filter;

Figure 8:
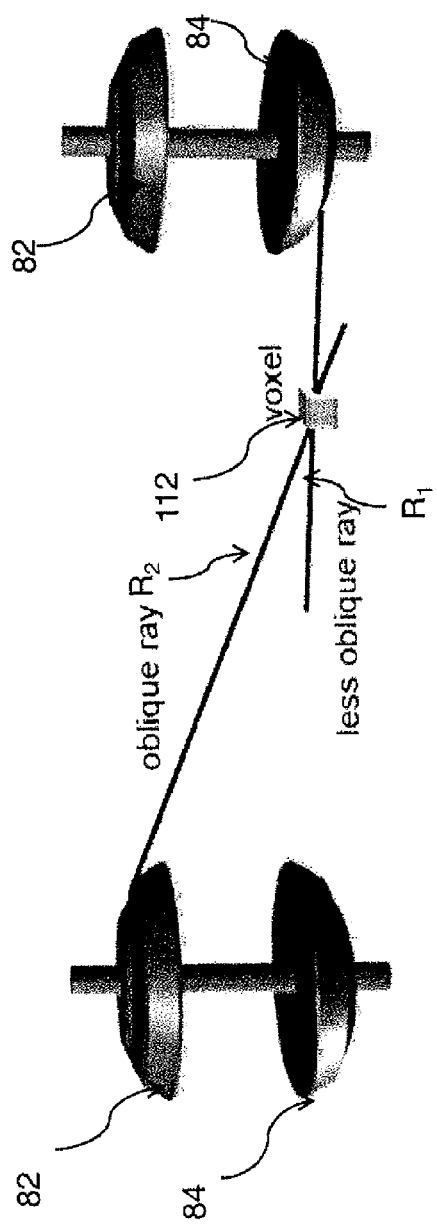
Figure 9:
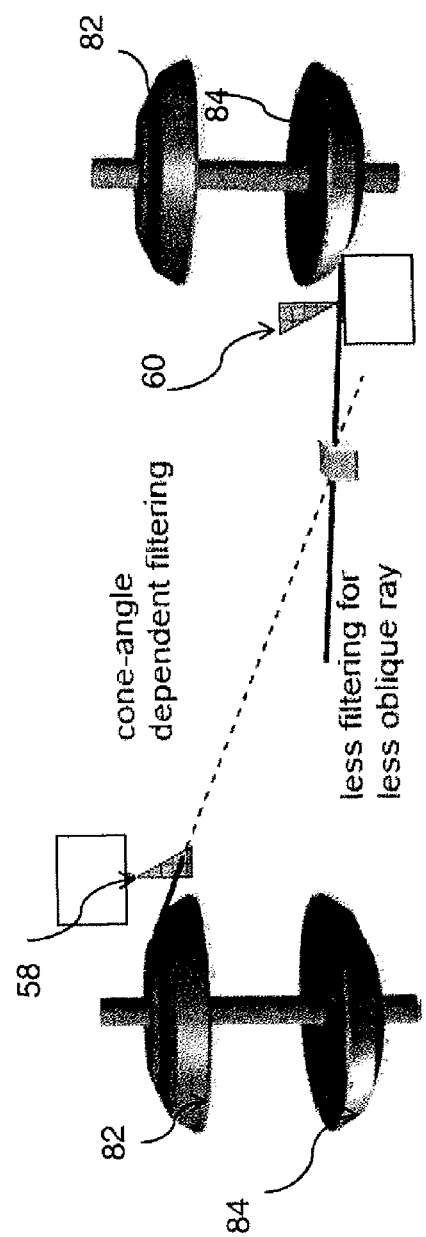
Figure 10:
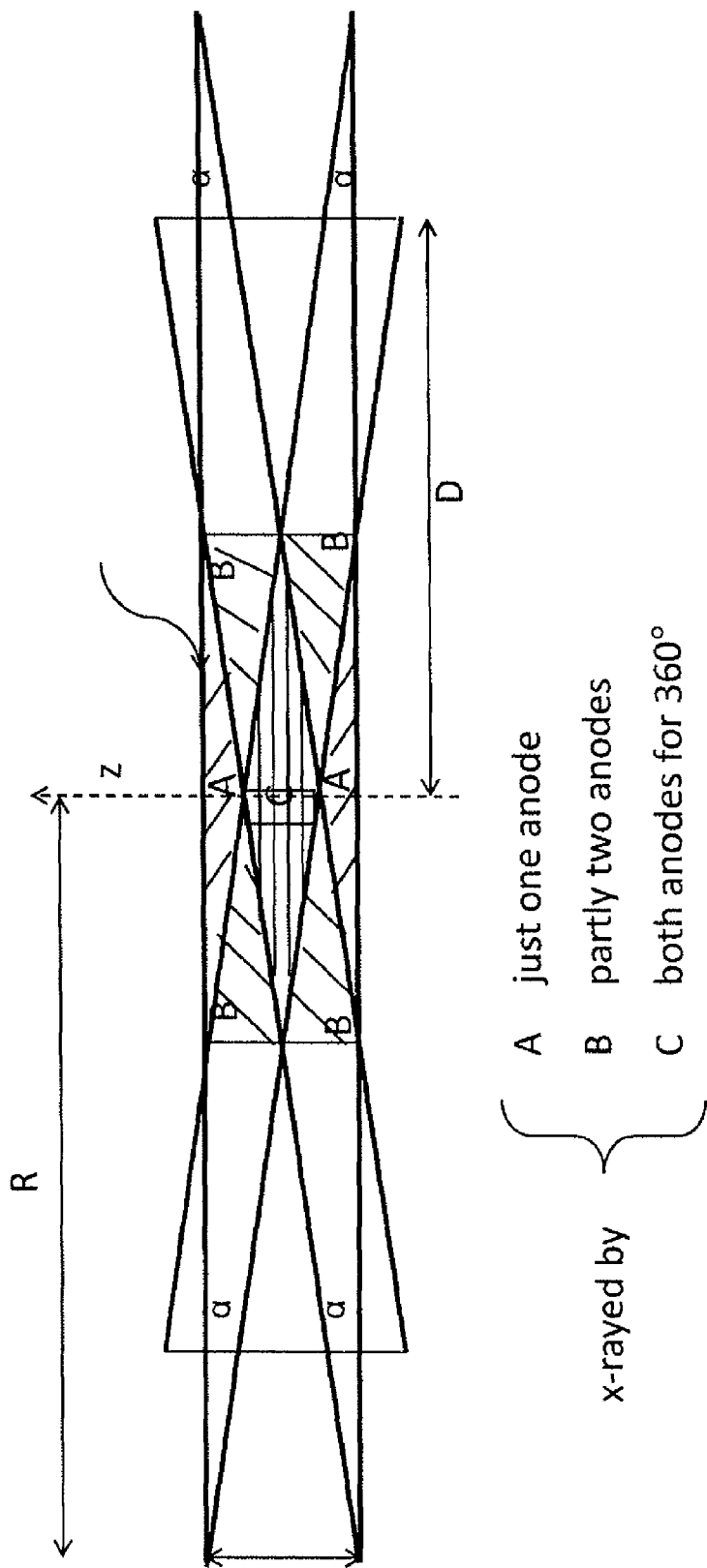

FIG. 8 schematically illustrates a stereo x-ray tube generating x-rays in the course of rotation;

FIG. 9 schematically illustrates a stereo x-ray tube generating x-rays in the course of rotation in which cone-angle dependent filtering attenuates the oblique x-ray more than less oblique x-ray;

FIG. 10 schematically illustrates dosage in a field of view during rotation of a stereo x-ray tube.

Figure 1:
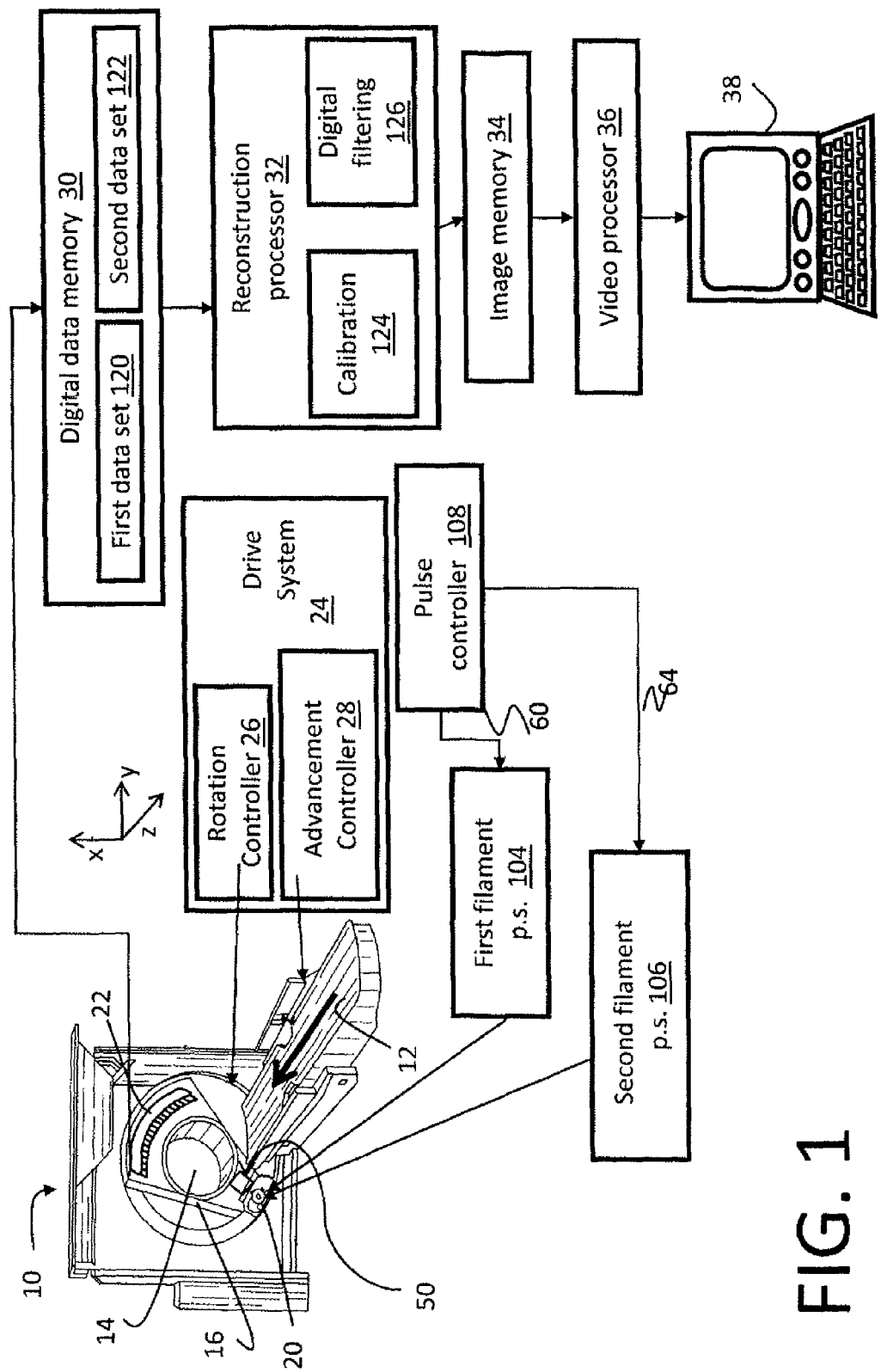
FIG. 1 illustrates a computed tomography imaging apparatus in accordance with one aspect of the exemplary embodiment.

With reference to FIG. 1, a computed tomography imaging scanner 10 includes a subject support 12 for moving a subject such as a medical patient, an item of luggage undergoing a security scan, or the like into or within an examination region 14 defined by a rotating gantry 16. A source of radiation, such as an x-ray tube 20 arranged on the gantry 16 projects at least one conically-shaped x-ray beam (a "cone beam") into the examination region 14 where it interacts with the imaging subject. Some portion of the x-rays are absorbed by the imaging subject to produce a generally spatially varying attenuation of the cone beam. A two-dimensional x-ray detector 22 disposed on the gantry 16 across the examination region 14 from the x-ray tube 20 measures the spatially-varying intensity of the x-ray beam after the x-ray beam passes through the examination region 14. Typically, the x-ray detector 22 is mounted on the rotating gantry 16. The detector 22 thus moves relative to the subject during imaging. In another suitable arrangement, the detector is arranged circumferentially on a stationary gantry surrounding the rotating gantry.

In helical computed tomography imaging, the gantry 16 rotates simultaneously with a linear motion of the subject support 12 in the z direction to effect a helical trajectory of the x-ray tube 20 about the examination region 14. For this application, a drive system 24 includes a rotation controller 26 for controlling gantry rotation and a linear advancement controller 28 for controlling the linear advancement. In axial computed tomography imaging, the gantry 16 rotates while the subject support 12 remains stationary to effect a circular trajectory of the x-ray tube 20 about the examination region 14. In volumetric axial imaging, the subject support 12 is repeatedly stepped linearly with an axial scan performed for each step to acquire multiple image slices along the axial direction.

Acquired imaging projection data with an index of the apex of the cone and of the trajectory within the cone is transmitted from the detector 22 and stored in a digital data memory 30. A reconstruction processor 32 reconstructs the acquired projection data, using filtered backprojection or another reconstruction method, to generate a three-dimensional image representation of the subject or of a selected portion thereof, which is stored in an image memory 34. The image representation is rendered or otherwise manipulated by a video processor 36 to produce a human-viewable image that is displayed on a graphical user interface 38 or another display device, printing device, or the like for viewing by an operator. In one embodiment, the graphical user interface 38 is programmed to interface a radiologist with the computed tomography scanner 10 to allow the radiologist to execute and control computed tomographic imaging sessions.

Figure 2:
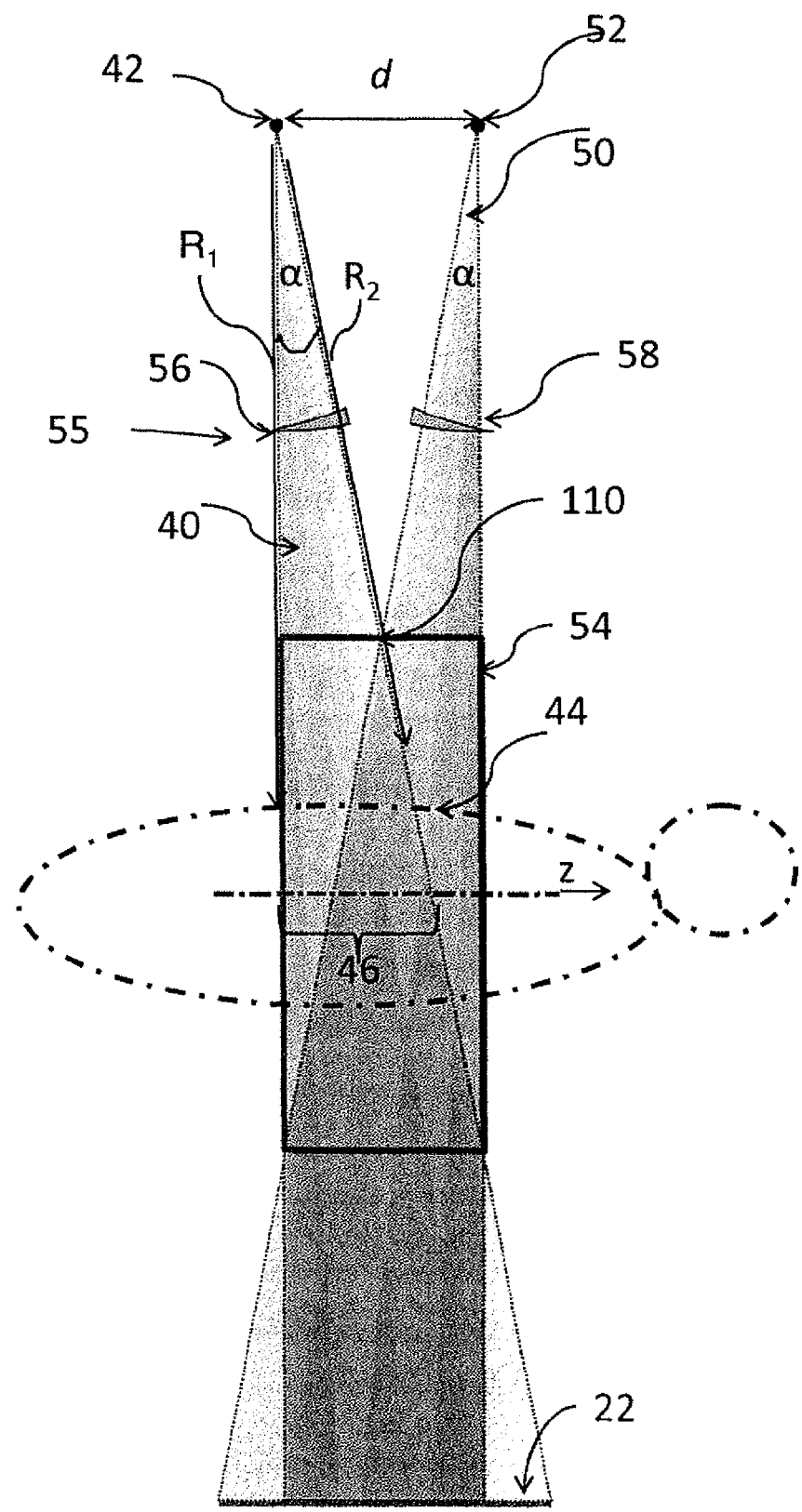
FIG. 2 illustrates dual cone beams irradiating a subject after attenuation by cone-angle dependent filters in accordance with another aspect of the exemplary embodiment.

In a cone beam 40, as illustrated schematically in cross sectional view in FIG. 2, the rays emanate from a focal point 42. The rays have a maximum beam angle α such that the rays pass through a subject 44 in a generally circular area 46 which has a central axis with a dimension in the z direction. The value of the maximum beam angle α determines the dimension of this area. FIG. 2 illustrates a dual beam arrangement in which first and second cone beams 40, 50 emanate from focal spots 42, 52 which are spaced, in the z direction by a distance d of, for example, about 10-20 cm, e.g., 12 cm. The two cone beams 40, 50 irradiate the same general area of the subject. As can be seen, the two beams 40, 50 overlap in coverage within a field of view 54 of the detector 22. In one embodiment, the beams 40, 50 are alternately pulsed such that the subject 44 and the detector 22 receive radiation from only one of the two beams 40, 50 at a given time. The pulse rate may be higher than the rotation speed of the gantry, for example, at least about 20,000 cycles/second. In one embodiment, the beam, and thus the focal spot is changed for each sampling period.

An advantage of a dual beam scanning system 10 as illustrated in FIG. 2 is that a larger amount of data can be acquired in each circular arc. This is particularly advantageous, for example, in cardiac scanning where the rhythmical beating of the heart muscles causes positions of features being scanned to change rhythmically during scanning. Another advantage of such a system is that a second pass cone beam artifact correction scheme may be employed.

The exemplary detector 22 has a radius of curvature equivalent to the distance to the two focal spots 42, 52 (both being equally spaced from the detector) and includes a plurality of segments. Each segment includes a plurality of detector elements which deliver a measurement value for pairs of rays (pi-partners) of the two radiation beams incident thereon. The accumulated measurement values, optionally after an initial preprocessing, form the data that is sent to the reconstruction processor 32.

With continued reference to FIG. 2, an attenuation system 55 is interposed between the focal spots 42, 52 and the examination region 14 for cone-angle dependent filtering of the cone beams 40, 50. In general, a method of computed tomography imaging which may be performed using the attenuation system 55 described herein includes projecting the first and second cone beams 40, 50 of radiation towards the examination region 14. Prior to reaching the examination region, the first and second cone beams are attenuated to form attenuated first and second cone-beams. The extent of attenuation is dependent on the cone angle. Radiation data is acquired from the examination region and an image is reconstructed, based on the radiation data.

With continued reference to FIG. 2, in one embodiment, the attenuation system 55 includes first and second filters 56, 58. The filters 56, 58 are formed of any suitable material capable of attenuating x-rays without significantly impacting the spectrum or angle of travel of the rays. Exemplary materials for forming the filters 56, 58 include aluminum, graphite, and perfluorinated polymers, such as Teflon®. The exemplary filters are physical (hardware) filters which variably attenuate radiation by virtue of their varying thickness (rather than software filters).

The illustrated cone beams 40, 50 are mirror images of each other and the exemplary filters 56, 58 are likewise mirror images of each other.

Each of the filters 56, 58 provides cone-angle dependent filtering of the respective beam 40, 50. Specifically, the filter 56, 58 attenuates the beam in the z-direction (linear scanning direction) progressively more as the cone angle of the ray increases. The cone angle is the angle of a given ray within the beam as determined from a plane in which the focal spot lies that is oriented normal (90° to the z direction. The attenuation by the filter 56, 58 is lowest for rays $R_1$, which approach the subject from the least oblique angle of the beam and highest for rays $R_2$, which approach the subject at the most oblique angle of the beam. In FIG. 2, the least oblique angle is at 0°, i.e., normal to the z direction and the most oblique angle is the maximum beam angle α from normal to the z direction.

Attenuation refers to the extent to which the intensity of the x-ray beam is reduced as it passes through the filter 56, 58. Thus, when the filter attenuation is lowest, the intensity of the radiation transmitted is a maximum, $I_{max}$. A maximum attenuation of the filter 56, 58 of the x-rays entering the field of view 54 corresponds to the minimum intensity of the transmitted radiation, $I_{min}$. The minimum attenuation (at $I_{max}$) provided by the filter 56, 58 for those x-rays entering the field of view may be about 0% (substantially no attenuation, thus $I_{max}=I_0$, the intensity of the radiation incident on the filter). The maximum attenuation, at $I_{min}$ provided by the filter 56, 58 for those x-rays entering the field of view may be up to 100% (full attenuation, no x-rays transmitted). In one embodiment, suitable for full 360° scanning, the attenuation at $I_{min}$ is 0% $I_{max}$. In other embodiments, suitable for partial scanning, $I_{min}$ is >0% of $I_{max}$, e.g., at least about 20% and in some embodiments, up to about 80% of $I_{max}$, e.g., about 50% $I_{max}$. Between the two extremes, the attenuation may vary linearly with the obliqueness of angle, as illustrated, for example, in FIG. 3. For example, if the maximum cone angle α is 15°, the intensity I at normal (0° is 100% ($I_{max}$), and at the full angle α of 15° is about 50% $I_{max}$ ($I_{min}$), then at 7.5° it is about 75% of $I_{max}$. In other embodiments, the transmission varies non-linearly, e.g., logarithmically, between the upper and lower values $I_{max}$ and $I_{min}$, as illustrated, for example, in FIG. 4.

Figure 5:
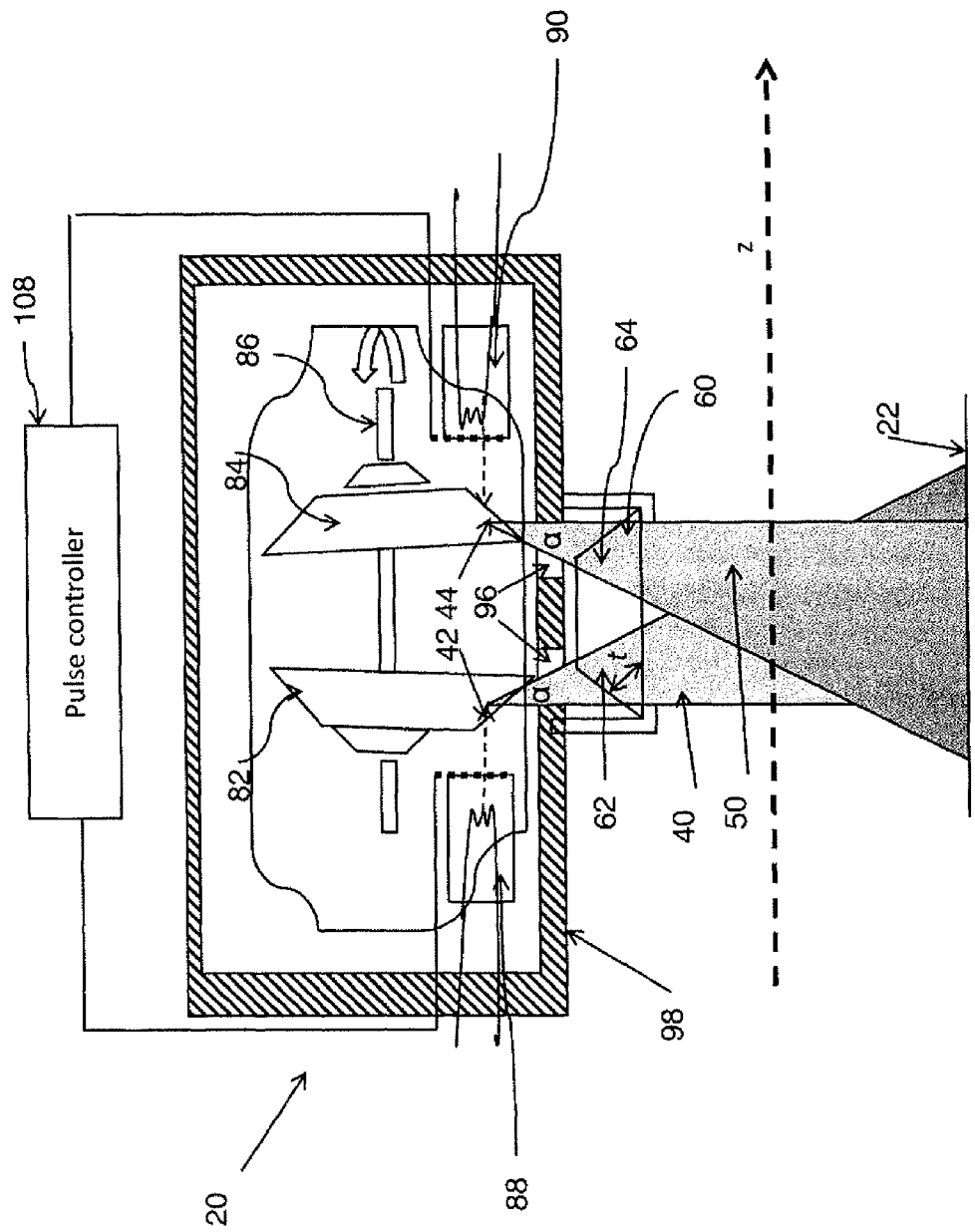
FIG. 5 is a schematic cross sectional view of a stereo x-ray tube with a cone-angle dependent filter in accordance with another aspect of the exemplary embodiment.

While FIG. 2 illustrates two spaced filters 56, 58, it is to be appreciated that a single combination filter 60 may alternatively be used, as illustrated in FIG. 5, which combines the functionality of the two filters 56, 58 described above. The combination filter 60 includes first and second filters 62, 64 which are joined together as one piece and perform in the same manner as the separate filters 56, 58.

In general, the attenuation provided by the filter 56, 58, 62, 64 is a function of the thickness t of the filter (as experienced by the rays passing through, i.e., in a direction which intersects the respective cone beam). Accordingly, in the exemplary embodiment, the thickness t of the filter changes in the z direction, with the greatest thickness occurring closest to the oblique rays and the least thickness, which may be at or close to zero, closest to the least oblique rays. In another embodiment, the concentration of an attenuating substance in the filter may be varied with the cone angle and thus the filter thickness need not change in the z direction.

As illustrated in FIG. 6, in perspective view, the cone-angle dependent filter 56, 58 is wedge shaped, with upper and lower surfaces 66, 68 that meet at a common edge 70 and a side surface 72, which extends between the upper and lower surfaces 66, 68 opposite the edge 70. The illustrated surfaces 66, 68 are curved, i.e., concave towards the focal spot, although in other embodiments, one or both surfaces 66, 68 are planar. The filter 56, 58 has a cross section which is uniform along its length/(i.e., in a direction extending perpendicular to the z direction). The combined filter 60 of FIG. 2 may be similarly configured, except that the two filters 62, 64 meet and thus have no side surface.

In another embodiment, shown in FIG. 7, a cone-angle dependent and bowtie combined filter 74 combines the combination filter 60 with a bowtie filter such that the combined filter 74 varies in thickness in both the z direction and xy plane. In this way, a subject to be irradiated, such as a human patient, whose cross section varies in the xy plane, may receive a dose which is more closely related to the cross sectional thickness of the subject. In another embodiment, the scanning apparatus 10 includes a bowtie filter that is separate from the cone-angle dependent filters 56, 58.

In the embodiment of FIG. 5, the dual beams 40, 50 are provided by a single, stereo x-ray tube 20. The stereo x-ray tube 20 tube includes a pair of commonly driven rotating tungsten anodes 82, 84. The illustrated anodes 82, 84 are mounted on the same rotatable shaft 86. It is also contemplated that the anodes may be mounted on separate shafts and may be separately driven within the x-ray tube 80. A cathode filament 88, 90, one for each anode 82, 84, is biased negatively with respect to the anode. A cathode cup 92, 94 partially surrounds the filament 88, 90 and is biased negatively to focus the electrons into an electron beam. Electrons generated at the cathode filament 88, 90 by thermionic emission are accelerated by the voltage difference and strike the respective rotating anode 82, 84, producing a beam of x-rays. The x-rays pass through each window 96 in a housing 98 of the x-ray tube 80 tube as a cone beam 40, 50. While FIG. 5 illustrates a double window 96, in one embodiment there is a common window, each beam 40, 50 having its own collimator. In the illustrated embodiment, the electrons from the opposed filaments 88, 90 are pulsed alternately, by alternately actuating a respective gate 100, 102, for example, by applying a voltage between electrodes mounted to the cathode cup 92, 94, which houses the respective filament 88, 90. The gates 100, 102, and/or filament power supplies 104, 106 (FIG. 1), are under the control of a common pulse controller 108.

As will be appreciated, in other embodiments, the two beams 40, 50 may be projected from focal spots 42, 52 which are in separate x-ray tubes, an anode of the first tube generating the first cone beam 40 and an anode of a second tube generating the second cone beam 50. In this embodiment, as in the stereo tube embodiment, the focal spots 42, 52 of the two anodes are aligned in the z direction.

In the embodiment of FIG. 5, the filters 62, 64 (or alternatively, filters 58, 60, or 74) are positioned exteriorly of the housing 98 to filter the respective beam 40, 50. The filters maintain a fixed orientation to the beam as the beam rotates around the subject. In one embodiment, the filters are fixedly mounted to the housing 98 or to another part of the x-ray tube 20 to minimize any relative motion between the focal spot 42, 52 and the respective filter 62, 64. In another embodiment, the filters 56, 58, 62, 64 are mounted to the gantry carrying the x-ray tube 20. In one embodiment, the position or orientation of the filter to the respective cone beam 40, 50 is adjustable to provide a different cone beam angle dependent filtering (e.g., a higher or lower maximum and/or minimum transmission). For example, in the embodiment of FIG. 2, filters 56, 58 may be movable perpendicular and/or parallel to the beam to vary the thickness experienced by the beam. In yet another embodiment, the filters may be replaceable with differently shaped filters, depending on desired maximum and/or minimum transmissions. For example, in the embodiment of FIG. 6, the height of the wall 72 may vary.

In general each filter 56, 58, 62, 64 only receives rays that are within a respective one of the cone beams 40, 50. Each filter 56, 58, 62, 64 thus serves to attenuate rays in only one of the beams 40, 50. For example, as shown in FIGS. 2 and 5, the filters 56, 58, 62, 64 are positioned intermediate the focal point 42, 52 of the respective beam and a point 110 at which the two beams 40, 50 begin to overlap one another.

As illustrated in FIG. 8, in a stereo cone-beam CT apparatus which lacks an attenuation system as described herein, multiple rays (pi-partners) are eligible for backprojection through the same voxel 112. The reconstruction processor weights the rays according to their angle. The oblique rays, such as ray $R_2$, are downweighted more strongly than less oblique rays, such as ray $R_1$. Both rays $R_1$, $R_2$ have the same intensity, although in the software reconstruction, the oblique ray $R_2$ will be virtually discarded due to its large cone angle. In the exemplary embodiment, the predictable fixed cone angle ranges of the stereo tube 20 that every voxel in the reconstruction grid is seen under facilitate the use of stationary hardware filters 56, 58, 62, 64 for ray intensity optimization. As illustrated in FIG. 9, the filters 56, 58 attenuate the rays $R_1$, $R_2$ according to their cone angle. The oblique ray $R_2$ receives more filtering than the less oblique ray $R_1$. The exemplary attenuation system 55 disclosed herein thus allows a reduction in the overall x-ray dose that a subject receives, while providing little or no adverse impact on the quality of the images generated during reconstruction, since the rays which are most attenuated in their intensity by the filters are those which tend to be downweighted in the software reconstruction.

In one embodiment, the maximum attenuation $T_{max}$ of the filter is a function of the coverage of the scan. For example, for a full 360° scan, the maximum attenuation may be higher than for a partial scan (less than 360°, e.g., 180°. This is because the dose distribution is not the same for a full scan and partial scan. In a full 360 degree scan, illustrated in FIG. 10, regions labeled A are x-rayed by just one of the anodes, regions B are partially x-rayed by two anodes and regions C are x-rayed by two anodes for the full 360°. As can be seen from FIG. 2, in a partial scan, the region of the field of view in which the two beams overlap receives a higher dose than the two adjacent regions which are only x-rayed by one beam. To reduce the impact of noise, therefore, for a partial scan of 180°, a maximum filter attenuation may be, for example, about 50%.

With reference again to FIG. 1, the imaging projection data acquired by the detector 22 for each cone beam pulse is processed by the reconstruction processor 32. In the exemplary embodiment, first and second data sets 120, 122, one corresponding to each cone beam 40, 50, are processed separately prior to reconstructing the image. The exemplary reconstruction processor 32 includes a calibration component 124 which allows baseline data acquired without a subject to be used in calibrating the imaging projection data. A digital filtering component 126 processes the imaging projection data to filter (e.g., downweight) the data for a voxel in the reconstruction grid according to the determined cone angle of the ray from which the data is derived. Since the calibration component 124 causes the scanner to measure the ratio of outgoing intensity $I_{out}$ (with subject) to incoming intensity $I_{in}$ (without subject), the influence of the cone-angle dependent filter is cancelled out and the line integrals that are used in the reconstruction algorithm are the same with or without the filter (other than in the extent of any noise). Accordingly, the reconstruction algorithm used to process the data need be no different from that which would be used without the attenuation system 55.

While the exemplary embodiment is discussed in terms of two cone beams 40, 50, it is to be appreciated that a single cone beam may be used. In other embodiments, more than two cone beams may irradiate the subject from respective focal spots which are linearly spaced in the z direction. Each of the plurality of cone beams may have its own associated cone-angle dependent filter.

While the exemplary embodiment is discussed in terms of a single detector 22, in another embodiment, a plurality of detectors, spaced in the z direction, e.g., one for each cone beam, may be employed.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A computed tomography apparatus comprising:
    a gantry which rotates on an axis of rotation around an examination region;
    a dual beam radiation source mounted on the gantry which dual beam radiation source propagates at least two cone-beams of radiation into the examination region, the dual beams of the dual beam radiation source being aligned in a direction parallel with the axis of rotation and oriented toward each other providing overlap of cone beams within the field of view;
    a common detector which detects the radiation from the two cone-beams which has passed through the examination region;
    a pulse controller which pulses the cone-beams of radiation alternatively; and
    an attenuation system interposed between the radiation sources and the examination region for cone-angle dependent filtering of the cone beams in an axial direction, the attenuation system including filters of thickness which increase in the direction of overlap of the dual beams in the field of view.

2. A computed tomography apparatus comprising:
    a gantry which rotates on an axis of rotation around an examination region;
    a common detector which has a field of view over which the detector detects radiation which has passed through the examination region;
    a dual beam radiation source mounted on the gantry which dual beam radiation source propagates at least two overlapping cone-beams of radiation into the examination region, each cone beam having an apex at a focal point of the cone beam, one face of the cone beam lying in a plane orthogonal to the axes of rotation to define one face of the field of view and another face extending across the field of view at an obtuse angle relative to the axis of rotation, wherein an attenuation system filters a first ray passing through a field of view of the detector within the examination region at an oblique angle more than a second ray passing through the field of view at a less oblique angle.

3. A computed tomography apparatus comprising:
    a gantry which rotates on an axis of rotation around an examination region;
    a dual beam radiation source mounted on the gantry which dual beam radiation source propagates at least two cone-beams of radiation into the examination region;
    a common detector which detects the radiation from the two cone-beams which has passed through the examination region;
    a pulse controller which pulses the cone-beams of radiation alternatively; and
    an attenuation system interposed between the radiation sources and the examination region for cone-angle dependent filtering of the cone beams, the attenuation system attenuating rays less as the ray direction is more orthogonal of the axis of rotation and attenuates more as the ray direction is less orthogonal of the axis of rotation.

4. The computed tomography apparatus of claim 3, wherein the dual beams of the dual beam radiation source are aligned in a direction parallel with the axis of rotation, and oriented toward each other providing overlap of cone beams within the field of view.

5. The computed tomography apparatus of claim 3, wherein the attenuation system includes filters of a thickness which varies in a scanning direction.

6. The computed tomography apparatus of claim 3, wherein the cone beams have a most oblique cone angle toward a center of the field of view and the attenuation system includes filters of thickness which have a maximum thickness at a most oblique cone angle of each cone beam.

7. The computed tomography apparatus of claim 3, wherein the maximum attenuation is at least 20%.

8. The computed tomography apparatus of claim 3, wherein the maximum attenuation is at least about 50%.

9. A computed tomography apparatus comprising:
    spaced radiation sources with first and second anodes aligned in a direction of scanning, each anode propagating a cone beam of radiation into an examination region, the cone beams being oriented toward each other such that the cone-beams overlap within the examination region;
    a common detector which detects the radiation which has passed through the examination region from both of the two anodes; and
    an attenuation system interposed between the anodes and the examination region, the attenuation system including a filter which attenuates the cone beams more towards a center of the examination region and less towards edges of the examination region.

10. The computed tomography apparatus of claim 9, wherein the first and second anodes are anodes of a common stereo x-ray tube.

11. The computed tomography apparatus of claim 9, further comprising a pulse controller for alternately pulsing the first and second anodes.

12. The computed tomography apparatus of claim 9, further comprising:
    a reconstruction processor which receives image data from the detector, the reconstruction processor digitally applying a cone angle-dependent weighting to the image data.

13. A method of computed tomography imaging comprising:
    projecting first and second cone beams of radiation from a single source towards an examination region;
    prior to the examination region:
    attenuating the first and second cone beams to form attenuated first and second cone-beams such that attenuation of each beam is greater toward a center of the examination region and less toward edges of the examination region; and acquiring radiation data from the examination region.

14. The method of claim 13, further comprising:
reconstructing an image based on the acquired radiation data.

15. The method of claim 14, further comprising:
down-weighting rays more oblique in an axial direction more strongly than rays less oblique in the axial direction in reconstructing the image.

16. The method of claim 13, further comprising:
aligning the cone beams along the direction of scanning, and orienting the cone beams toward each other providing overlap of within the field of view;
wherein the attenuating includes passing each of the cone beams through a respective filter of varying thickness.

17. The method of claim 13, wherein the attenuating includes passing each of the cone beams through a respective filter of varying thickness.

18. An imaging system comprising: at least two x-ray sources displaced along a z-axis, the at least two x-ray sources configured to alternately emit x-ray beams; an x-ray detector assembly configured to detect the x-ray beams; and an attenuation filter mounted proximate the at least two x-ray sources, the attenuation filter configured to provide different amounts of x-ray attenuation to the x-ray beams along the z-axis.

19. The imaging system of claim 18, wherein the attenuation filter comprises at least one of a substantially triangular shaped portion and a curved portion along the z-axis.

20. The imaging system of claim 18, wherein the attenuation filter provides a greater amount of x-ray attenuation to the x-ray beams proximate a central portion of the attenuation filter along the z-axis and a relatively lesser amount of x-ray attenuation to the x-ray beams proximate outer portions of the attenuation filter along the z-axis.

21. The imaging system of claim 18, wherein the attenuation filter comprises a triangular shaped portion along the z-axis, and wherein a peak of the triangular shaped portion provides greater x-ray attenuation than non-peak portions.

22. The imaging system of claim 18, wherein the attenuation filter comprises one of a triangular shaped portion and a convexly curved portion along a y-z plane and a "U" shaped portion along an x-y plane.

23. The imaging system of claim 18, wherein the x-ray beams partially overlap each other to form an overlapping region within an imaging area, the attenuation filter further configured to provide greater x-ray attenuation within the overlapping region.

24. The imaging system of claim 18, further comprising a processor configured to receive image data based on the x-ray beams, the processor further configured to combine the image data to form a combined image.

25. A method for at least partially compensating for increased x-ray flux from multiple x-ray sources mounted along a z-axis, the method comprising: transmitting x-ray beams alternately from at least two adjacent x-ray sources, the x-ray beams forming an overlapping region within an imaging area; and positioning an attenuation filter between the at least two adjacent x-ray sources and an x-ray detector assembly, the attenuation filter providing different amounts of x-ray attenuation to the x-ray beams along the z-axis.

26. The method of claim 25, wherein the attenuation filter has a higher attenuation coefficient corresponding to the overlapping region and a lower attenuation coefficient corresponding to non-overlapping regions within the imaging area.

27. The method of claim 25, wherein the attenuation filter comprises a central portion and outer portions with respect to the z-axis, the central portion providing a higher level of x-ray attenuation than the outer portions.

28. The method of claim 25, wherein the amount of x-ray attenuation provided is based on a location of the overlapping region.

29. The method of claim 25, wherein the transmitting further comprises transmitting x-ray beams from two other adjacent x-ray sources, the x-ray beams forming a second overlapping region within the imaging area, the attenuation filter further providing different amounts of x-ray attenuation along the z-axis based on the overlapping region and the second overlapping region.

30. The method of claim 25, wherein the attenuation filter comprises at least one substantially triangular shaped portion along the z-axis that has a peak, and the positioning further comprises positioning the peak along the z-axis between two adjacent x-ray sources.

31. A computed tomography (CT) imaging system comprising: at least two x-ray sources aligned along a z-axis; a detector assembly positioned to detect x-rays beams from the at least two x-ray sources, wherein the at least two x-ray sources are configured to alternately emit x-ray beams that partially overlap within an overlapping region of an imaging area, the imaging area located between the at least two x-ray sources and the detector assembly; and an attenuation filter positioned between the at least two x-ray sources and the imaging area, the attenuation filter configured to provide relatively higher x-ray attenuation along the z-axis corresponding to the overlapping region and relatively lower x-ray attenuation along the z-axis corresponding to at least one non-overlapping region of the imaging area.

32. The system of claim 31, wherein the attenuation filter is configured to attenuate the x-ray beams using a substantially triangular shape along the z-axis, and wherein a peak of the triangular shape provides a greatest level of x-ray attenuation.

33. The system of claim 31, further comprising a computer operationally coupled to the at least two x-ray sources and the detector assembly, wherein the computer is configured to receive projection data associated with each of the x-ray beams from the at least two x-ray sources, the computer further configured to combine the projection data into a combined image.

34. The system of claim 31, wherein the attenuation filter comprises a plurality of triangular shaped portions along the z-axis, each of the plurality of triangular shaped portions having a peak, and wherein the peaks of the triangular shaped portions provide greater x-ray attenuation than non-peak portions.

35. The system of claim 31, wherein the attenuation filter comprises at least one of a triangular shaped portion and a curved portion along a y-z plane and a substantially "U" shaped portion along an x-y plane.

36. The system of claim 31, wherein the attenuation filter comprises at least one of aluminum, aluminum alloy, copper and graphite.

37. The system of claim 31, wherein a thickness at a peak of the attenuation filter along the z-axis is between three and four millimeters greater than thicknesses at outer edges of the attenuation filter.

* * * * *